US008530632B2

(12) United States Patent
Tijsma et al.

(10) Patent No.: US 8,530,632 B2
(45) **Date of Patent: *Sep. 10, 2013**

(54) CHITOSAN-CONTAINING PROTECTIVE COMPOSITION

(75) Inventors: Edze Jan Tijsma, Middelburg (NL); Maria Nieves Gonzalez, Alcorcon (ES); Matthew Franco Myntti, Jacksonville, FL (US); Brian Vaccaro, Pointe Vedra Beach, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 339 days.

This patent is subject to a terminal disclaimer.

(21) Appl. No.: 12/429,150

(22) Filed: Apr. 23, 2009

(65) Prior Publication Data

US 2009/0291912 A1 Nov. 26, 2009

Related U.S. Application Data

(60) Provisional application No. 61/047,590, filed on Apr. 24, 2008, provisional application No. 61/105,380, filed on Oct. 14, 2008.

(51) Int. Cl.
*C08B 37/08* (2006.01)

(52) U.S. Cl.
CPC .................................... *C08B 37/003* (2013.01)
USPC ............................................ 536/20; 536/55.1

(58) Field of Classification Search
None
See application file for complete search history.

(56) References Cited

U.S. PATENT DOCUMENTS

| | | | | |
|---|---|---|---|---|
| 3,184,385 | A | 5/1965 | Anderson | |
| 3,914,214 | A | 10/1975 | Trimnell et al. | |
| 3,989,044 | A | 11/1976 | Meierhoefer | |
| 4,604,384 | A | 8/1986 | Smith et al. | |
| 4,659,700 | A | 4/1987 | Jackson | |
| 4,895,724 | A | 1/1990 | Cardinal et al. | |
| 4,960,413 | A | 10/1990 | Sagar et al. | |
| 4,983,385 | A | 1/1991 | Hasegawa et al. | |
| 5,308,546 | A | 5/1994 | Hansen et al. | |
| 5,312,324 | A | 5/1994 | Walthour | |
| 5,318,780 | A | 6/1994 | Viegas et al. | |
| 5,550,189 | A | 8/1996 | Qin et al. | |
| 5,623,064 | A | 4/1997 | Vournakis et al. | |
| 5,667,778 | A | 9/1997 | Atala | |
| 5,679,658 | A | 10/1997 | Elson | |
| 5,688,522 | A | 11/1997 | Hardy | |
| 5,723,144 | A | 3/1998 | Hardy | |
| 5,747,475 | A | 5/1998 | Nordquist et al. | |
| 5,820,608 | A | 10/1998 | Luzio et al. | |
| 5,840,341 | A | 11/1998 | Watts et al. | |
| 5,993,846 | A | 11/1999 | Friedman et al. | |
| 6,096,018 | A | 8/2000 | Luzio et al. | |
| 6,123,965 | A | 9/2000 | Jacob et al. | |
| 6,224,893 | B1 | 5/2001 | Langer et al. | |
| 6,290,712 | B1 | 9/2001 | Nordquist et al. | |
| 6,320,029 | B1 | 11/2001 | Miekka et al. | |
| 6,334,968 | B1 | 1/2002 | Shapiro et al. | |
| 6,342,251 | B1 | 1/2002 | Illum et al. | |
| 6,344,488 | B1 | 2/2002 | Chenite et al. | |
| 6,346,272 | B1 | 2/2002 | Viegas et al. | |
| 6,417,347 | B1 | 7/2002 | Herrmann et al. | |
| 6,458,889 | B1 | 10/2002 | Trollsas et al. | |
| 6,514,522 | B2 | 2/2003 | Domb | |
| 6,545,042 | B2 | 4/2003 | Sung et al. | |
| 6,566,406 | B1 | 5/2003 | Pathak et al. | |
| 6,599,627 | B2 | 7/2003 | Yeo et al. | |
| 6,602,952 | B1 | 8/2003 | Bentley et al. | |
| 6,632,423 | B2 | 10/2003 | Jafari et al. | |
| 6,664,301 | B1 | 12/2003 | Kross | |
| 6,706,690 | B2 | 3/2004 | Reich et al. | |
| 6,719,987 | B2 | 4/2004 | Burrell et al. | |
| 6,806,260 | B1 | 10/2004 | Hirofumi et al. | |
| 6,809,085 | B1 | 10/2004 | Elson et al. | |
| 6,835,389 | B1 | 12/2004 | Dohi et al. | |
| 6,989,373 | B2 | 1/2006 | Des Rosiers | |
| 6,991,652 | B2 | 1/2006 | Burg | |
| 7,053,068 | B2 | 5/2006 | Prinz | |
| 7,070,582 | B2 | 7/2006 | Freyman et al. | |
| 7,087,249 | B2 | 8/2006 | Burrell et al. | |
| 7,098,194 | B2 | 8/2006 | Chenite et al. | |
| 7,125,860 | B1 | 10/2006 | Renier et al. | |
| 7,195,675 | B2 | 3/2007 | Okazaki et al. | |
| 7,229,966 | B2 | 6/2007 | Quay et al. | |
| 7,354,600 | B1 | 4/2008 | Bernkop-Schnürch | |
| 7,740,883 | B2 * | 6/2010 | Borbely et al. | 424/492 |
| 7,834,065 | B2 * | 11/2010 | Nakajima et al. | 523/111 |
| 2002/0042473 | A1 | 4/2002 | Trollsas et al. | |
| 2002/0064580 | A1 * | 5/2002 | Gord et al. | 426/105 |

(Continued)

FOREIGN PATENT DOCUMENTS

| | | | |
|---|---|---|---|
| CA | 2 348 842 | A1 | 5/2000 |
| CA | 2 574 232 | | 1/2006 |

(Continued)

OTHER PUBLICATIONS

Sakaira, machine translation of JP2002327388, retrieved from the internet <http://dossier1.ipdl.inpit.go.jp/AIPN/odse_top_fwi.ipdl?N0000=7401> on Jun. 29, 2011, pp. 1-13.*

(Continued)

*Primary Examiner* — Eric S Olson
(74) *Attorney, Agent, or Firm* — IPLM Group, P.A.

(57) ABSTRACT

Body tissue and structures may be protected using a fluid containing a mixture of partially crosslinked polysaccharide and a further crosslinker. The mixture desirably is sprayable, forms a fluid protective layer via in situ crosslinking, desirably does not drip or run from a treatment site, and may avoid the use of more rapidly curing but potentially less bioacceptable crosslinkers at the treatment site.

21 Claims, 3 Drawing Sheets

(56) References Cited

U.S. PATENT DOCUMENTS

| | | | | |
|---|---|---|---|---|
| 2002/0193812 | A1 | 12/2002 | Patel et al. | |
| 2003/0073663 | A1* | 4/2003 | Wiseman et al. | 514/54 |
| 2004/0029855 | A1 | 2/2004 | Klaveness et al. | |
| 2004/0127698 | A1 | 7/2004 | Tsai et al. | |
| 2005/0002893 | A1* | 1/2005 | Goldmann | 424/70.27 |
| 2005/0019404 | A1 | 1/2005 | Sung et al. | |
| 2005/0069572 | A1 | 3/2005 | Williams et al. | |
| 2005/0096282 | A1 | 5/2005 | Lewin et al. | |
| 2005/0176620 | A1 | 8/2005 | Prestwych et al. | |
| 2005/0208122 | A1 | 9/2005 | Allen et al. | |
| 2005/0238702 | A1 | 10/2005 | Ishihara et al. | |
| 2006/0134185 | A1 | 6/2006 | Odermatt et al. | |
| 2006/0147539 | A1 | 7/2006 | Sung et al. | |
| 2006/0172000 | A1* | 8/2006 | Cullen et al. | 424/445 |
| 2006/0234871 | A1* | 10/2006 | Dalrymple et al. | 507/211 |
| 2006/0292030 | A1 | 12/2006 | Odermatt et al. | |
| 2007/0031467 | A1 | 2/2007 | Abrahams et al. | |
| 2007/0031474 | A1 | 2/2007 | Tayot | |
| 2007/0048291 | A1 | 3/2007 | Mang et al. | |
| 2007/0066924 | A1 | 3/2007 | Hopman et al. | |
| 2007/0087059 | A1 | 4/2007 | Everaerts et al. | |
| 2007/0098675 | A1 | 5/2007 | Elisseeff et al. | |
| 2007/0110788 | A1 | 5/2007 | Hissong et al. | |
| 2007/0191963 | A1 | 8/2007 | Winterbottom et al. | |
| 2007/0202142 | A1 | 8/2007 | Laugier et al. | |
| 2007/0243130 | A1 | 10/2007 | Chen et al. | |
| 2007/0243131 | A1 | 10/2007 | Chen et al. | |
| 2007/0264310 | A1 | 11/2007 | Hissong et al. | |
| 2008/0031854 | A1 | 2/2008 | Prestwich et al. | |
| 2008/0069857 | A1* | 3/2008 | Yeo et al. | 424/426 |
| 2008/0075657 | A1 | 3/2008 | Abrahams | |
| 2008/0317765 | A1 | 12/2008 | Izraeli et al. | |
| 2008/0319101 | A1 | 12/2008 | Nakajima et al. | |
| 2009/0005339 | A1 | 1/2009 | Scholz et al. | |
| 2009/0010982 | A1 | 1/2009 | Abrahams et al. | |
| 2009/0041814 | A1 | 2/2009 | Nanbu | |
| 2009/0062233 | A1 | 3/2009 | Ji et al. | |

FOREIGN PATENT DOCUMENTS

| | | | |
|---|---|---|---|
| CN | 1872351 | A | 12/2006 |
| EP | 0 815 879 | A2 | 1/1998 |
| EP | 1 228 771 | A1 | 8/2002 |
| EP | 1 880 738 | A1 | 1/2008 |
| FR | 2 889 449 | A1 | 8/2005 |
| JP | 2002-327338 | * | 11/2002 |
| JP | 2008-247975 | | 10/2008 |
| JP | 2008-285611 | | 11/2008 |
| WO | WO 92/16245 | | 10/1992 |
| WO | WO 93/21906 | | 11/1993 |
| WO | WO 96/14828 | | 5/1996 |
| WO | WO 98/19718 | | 5/1998 |
| WO | WO 98/31712 | A2 | 7/1998 |
| WO | WO 99/01166 | | 1/1999 |
| WO | WO 99/07416 | | 2/1999 |
| WO | WO 00/40252 | | 7/2000 |
| WO | WO 01/00246 | A2 | 1/2001 |
| WO | WO 03/020771 | A1 | 3/2003 |
| WO | WO 03/057274 | A2 | 7/2003 |
| WO | WO 03/080135 | A1 | 10/2003 |
| WO | WO 2004/026200 | A | 4/2004 |
| WO | WO 2007/059390 | A1 | 5/2007 |
| WO | WO 2007/071375 | A | 6/2007 |
| WO | WO 2008/005671 | A2 | 1/2008 |
| WO | WO 2008/008857 | A | 1/2008 |
| WO | WO 2008/067655 | A | 6/2008 |
| WO | WO 2008/067655 | A1 | 6/2008 |
| WO | WO 2008/097317 | A | 8/2008 |
| WO | WO 2009/028965 | A1 | 3/2009 |

OTHER PUBLICATIONS

Definition of derivative, retrieved from Merriam-Webster online dictionary <<http://www.meriamwebster.com/dictionary/derivative>> on Apr. 6, 2011, 2 pages.*

Leitner et al., "*Thiomers in noninvasive polypeptide delivery: in vitro and in vivo characterization of a polycarbophilcysteine/glutathione gel formulation for human growth hormone*", J. Pharm. Sci, 93, 1682-1691 (2004).

Bromberg, "*Intelligent Polyelectrolytes and Gels in Oral Drug Delivery*" Department of Chemical Engineering, Massachusetts Institute of Technology, Cambridge, Massachusetts, U.S.A. in Current Pharmaceutical Biotechnology, 4, 339-349 (2003).

Prestwich et al., "*3-D culture in synthetic extracellular matrices: New tissue models for drug toxicology and cancer drug delivery*", Advances in Enzyme Regulation, Elsevier Ltd., 47, 196-207 (2007).

Kast et al., "*Thiolated polymers-thiomers: development and in vitro evaluation of chitosan-thioglycolic acid conjugates*", Biomaterials, Elsevier Science Publishers, 22, 2345-2352 (2001).

Fwu-Long et al., *pH-sensitive behavior of two-component hydrogels composed of N,O-carboxymethal chitosan and alginate*, J. Biomater, Sci. Polymer Edn., vol. 16, No. 11, 1333-1345 (2005).

Fwu-Long et al., *Synthesis and characterization of biodegradable TPP/genipin co-crosslinked chitosan gel beads*, Polymer, 44, 6521-6530 (2003).

Reyes et al., *A Modified Chondroitin Sulfate Aldehyde Adhesive for Sealing Corneal Incisions*, Investigative Ophthalmology & Visual Science, vol. 6, No. 4, 1247-1250 (Apr. 2005).

Mi et al., *Synthesis and Characterization of a Novel Chitosan-Based Network Prepared Using Naturally-Occurring Crosslinker*, J Polym Sci, Part A: Polym Chem, 38, 2804-2814 (2000).

Mi et al., *Synthesis and characterization of biodegradable TPP/genipin co-crosslinked chitosan gel beads*, Polymer, 44, 6521-30 (2003).

Roldo et al., *Mucoadhesive thiolated chitosans as platforms for oral controlled drug delivery: synthesis and in vitro evaluation*, European Journal of Pharmaceutics and Biopharmaceutics, 57, 115-121 (2004).

Krauland et al., *Viscoelastic Properties of a New in situ Gelling Thiolated Chitosan Conjugate*, Drug Development and Industrial Pharmacy, 31, 885-893 (2005).

Bernkop-Schnürch, *Thiomers: A new generation of mucoadhesive polymers*, Advanced Drug Delivery Reviews, 57, 1569-1582 (2005).

Bernkop-Schnürch et al., *Thiomers: Preparation and in vitro evaluation of a mucoadhesive nanoparticulate drug delivery system*, International journal of Pharmaceutics, 317, 76-81 (2006).

Weng et al., *Rheological Characterization of in Situ Crosslinkable Hydrogels Formulated from Oxidized Dextran and N-Carboxyethyl Chitosan*, Biomacromolecules, 8, 1109-1115 (2007).

Wang et al., *Multifunctional chondroitin sulphate for cartilage tissue-biomaterial integration*, nature materials, vol. 6, 385-392 (May 2007).

Aspden et al, *Chitosan as a Nasal Delivery System: The Effect of Chitosan on In Vitro and In Vivo Mucociliary Transport Rates in Human Turbinates and Volunteers*, J Pharm Sci, 86, 4, 509-513 (1997).

Costain et al., *Prevention of postsurgical adhesions with N,O-carboxymethyl chitosan: Examination of the most efficacious preparation and the effect of N,O-carboxymethyl chitosan on postsurgical healing*, Surgery, 121, 3, 314-319 (1997).

Hong et al., *Covalently crosslinked chitosan hydrogel: Properties of in vitro degradation and chondrocyte encapsulation*, Acta Biomaterialia, 3, 1, 23-31 (2007).

Park et al., *Crosslinked hydrogels for tympanic membrane repair*, Otolaryngology—Head and Neck Surgery, 135, 887-883 (2006).

Carlsson et al., *Immobilization of Urease by Thiol-Disulphide Interchange with Concomitant Purification*, Eur. J. Biochem, 44, 189-194 (1974).

Hoober et al., *Sulfhydryl Oxidase from Egg White*, The Journal of Biological Chemistry, vol. 274, No. 32, Issue of Aug. 6, 22147-22150 (1999).

Barbucci et al., *Hyaluronic acid hydrogel in the treatment of osteoarthritis*, Biomaterials 23, 4503-4513 (2002).

Anonymous, "*Chitoflex™—Surgical*", Sep. 2007, 2 pages, retrieved from the Internet at: www.alltracel.com/Portals/1/ChitoFlex%20-%20Surgical%20Product%20Overview%20Brochure.pdf.

Szczubialka et al., "*Novel drug carrier—Chitosan gel microspheres with covalently attached nicotinic acid*", Journal of Controlled Release, Elsevier, vol. 16, No. 2, e13-e15, XP005794286 (2006).

Mwale Fackson et al., "*Biological evaluation of chitosan salts cross-linked to genipin as a cell scaffold for disk tissue engineering*", Tissue Engineering, vol. 11, No. 1-2, 130-140, XP002518499 (2005).

Bernkop-Schnürch, A., et al., "*Improvement in the mucoadhesive properties of alginate by the covalent attachment of cysteine*", Journal of Controlled Release, Elsevier, 71, 277-285 (2001).

Athanasiadis, Theo et al., "*Effects of a novel chitosan gel on mucosal wound healing following endoscopic sinus surgery in a sheep model of chronic rhinosinusitis*", The Laryngoscope, vol. 118, No. 6, 1088-1094, XP002535403 (2008).

Liu, G. et al., "Synthesis and Characterization of Chitosan/Dextran-Based Hydrogels for Surgical Use", Macromol. Symp., 279, pp. 151-157, (2009).

Haugh, M.G. et al., "The effect of dehydrothermal treatmetn on the mechanical and structural properties of collagen-GAG scaffolds", Royal College of Surgeons in Ireland, Department of Anatomy, 23 pages, (2009).

Ringe, K. et al., "Nanoparticle Drug Delivery to the Brain", Encyclopedia of Nanoscience and Nanotechnology, vol. 7, pp. 91-104, (2004).

Kumar et al., "Chitosan Chemistry and Pharmaceutical Perspectives", Chem. Rev. 104, pp. 6017-6084 (2004).

NovaMatrix Ultrapure Biopolymer Systems catalog and prices, 4 pages (Sep. 2011).

Wang, et. al, "The synthesis and characterization of novel bioadhesive material thiolated chitosan", Chemical Journal of Chinese Universities, No. 1, vol. 29, January, pp. 206-211 (2008).

Huang et al., "The Application and Development of New Crosslinking Agent Genipin in Biomedicine", Shanghai Biomedical Engineering Journal, No. 1, vol. 24, pp. 21-25 (2003).

NovaMatrix Ultrapure Biopolymer Systems, "*Chitosan*", Data Sheets, 2 pp. (2011).

Higashiyama, Takanobu, "*Novel functions and applications of trehalose*", Pure Appl. Chem., vol. 74, No. 7, pp. 1263-1269 (2002).

Bernkop-Schnürch, A., et al., "*Thiolated polymers-thiomers: synthesis and in vitro evaluation of chitosan -2- iminothiolane conjugates*", International Journal of Pharmaceutics, vol. 260, Issue 2, (Jul. 24, 2003).

* cited by examiner

CHITOSAN-CONTAINING PROTECTIVE COMPOSITION

CROSS REFERENCE TO RELATED APPLICATION

This application claims priority from U.S. provisional applications Ser. No. 61/047,590 filed Apr. 24, 2008 and Ser. No. 61/105,380 filed Oct. 14, 2008, the disclosures of which are incorporated herein by reference.

FIELD OF THE INVENTION

This invention relates to chitosans and to materials for use in or on tissue and structures in the ears, nose, throat, limbs and spinal column.

BACKGROUND

Various chitosan-containing materials and chitosan derivatives have been used for surgical repair or drug delivery. Documents relating to such materials or derivatives include U.S. Pat. No. 6,514,522 (Domb), U.S. Pat. No. 6,602,952 B1 (Bentley et al.) and U.S. Pat. No. 7,053,068 B2 (Prinz), U.S. Patent Application Publication No. US 2005/0238702 A1 (Ishihara et al.), Canadian Patent Application No. 2 348 842 A1 (Bernkop-Schnürch), Published PCT Application No. WO 98/31712 A2 (B.F. Goodrich Co.), Aspden et al, *Chitosan as a Nasal Delivery System: The Effect of Chitosan on In Vitro and In Vivo Mucociliary Transport Rates in Human Turbinates and Volunteers*, J Pharm Sci, 86, 4, 509-513 (1997), Costain et al., *Prevention of postsurgical adhesions with N,O-carboxymethyl chitosan: Examination of the most efficacious preparation and the effect of N,O-carboxymethyl chitosan on postsurgical healing*, Surgery, 121, 3, 314-319 (1997), Mi et al., *Synthesis and Characterization of a Novel Chitosan-Based Network Prepared Using Naturally-Occurring Crosslinker*, J Polym Sci, Part A: Polym Chem, 38, 2804-2814 (2000), Mi et al., *Synthesis and characterization of biodegradable TPP/genipin co-crosslinked chitosan gel beads*, Polymer, 44, 6521-30 (2003), Roldo et al., *Mucoadhesive thiolated chitosans as platforms for oral controlled drug delivery: synthesis and in vitro evaluation*, European Journal of Pharmaceutics and Biopharmaceutics, 57, 115-121 (2004), Krauland et al., *Viscoelastic Properties of a New in situ Gelling Thiolated Chitosan Conjugate*, Drug Development And Industrial Pharmacy, 31, 885-893 (2005), Bernkop-Schnürch, *Thiomers: A new generation of mucoadhesive polymers*, Advanced Drug Delivery Reviews, 57, 1569-1582 (2005), Bernkop-Schnürch et al., *Thiomers: Preparation and in vitro evaluation of a mucoadhesive nanoparticulate drug delivery system*, International journal of Pharmaceutics, 317, 76-81 (2006), Hong et al., *Covalently crosslinked chitosan hydrogel: Properties of in vitro degradation and chondrocyte encapsulation*, Acta Biomaterialia, 3, 1, 23-31 (2007) and Weng et al., *Rheological Characterization of in Situ Crosslinkable Hydrogels Formulated from Oxidized Dextran and N-Carboxyethyl Chitosan*, Biomacromolecules, 8, 1109-1115 (2007).

SUMMARY OF THE INVENTION

Chitosan and its derivatives may be solubilized in aqueous solutions. In order to spray-apply such solutions (e.g., through a spray nozzle or needle), low viscosity is required. Hydration or dilution may occur once the spray-applied solution reaches an intended treatment site, thereby further reducing viscosity. A spray-applied solution may accordingly drain from, be quickly resorbed by or otherwise prematurely disappear from a desired treatment site. Chitosans may be crosslinked prior to delivery in order to reduce the likelihood of their premature disappearance, but the crosslinked polymers may be too viscous for spray application. Chitosans may also be crosslinked in situ by combining them with a crosslinker following delivery, but the crosslinking reaction may proceed too slowly for practical use unless potentially harmful crosslinking agents are employed.

The present invention provides, in one aspect, a two-part composition, the first part comprising a partially crosslinked polysaccharide and the second part comprising a further crosslinker for the polysaccharide, wherein the polysaccharide or further crosslinker comprise chitosan or a chitosan derivative and the composition when hydrated and mixed can be delivered as a fluid through a spray applicator to provide a thin, conformal protective layer on a body temperature substantially vertical skin surface. The disclosed composition desirably is packaged in a multicomponent spray dispenser with the chitosan-containing part in dry (e.g., lyophilized) form, hydrated at or close in time to the point of use, and quickly mixed with the further crosslinker-containing part and spray-applied to a desired target area on body tissue or body structure. The mixed parts are a fluid (viz., ungelled) when the mixture travels through the spray applicator, and may eventually form a gel (e.g., by the time it lands on the target area or a few minutes thereafter) or may remain a fluid when on the target area.

The invention provides in another aspect a protective layer on a body temperature surface, the layer comprising an initially fluid mixture of a partially crosslinked polysaccharide and a further crosslinker for the polysaccharide, wherein the polysaccharide or further crosslinker comprise chitosan or a chitosan derivative and the partially crosslinked polysaccharide was partially crosslinked before mixture with the further crosslinker. The layer may be an initially fluid layer, or may be an initially fluid mixture that forms a gel by the time the layer and body temperature surface come into contact with one another.

The invention provides in another aspect a method for treating body tissue or structure, which method comprises:

a) mixing a two-part composition, the first part comprising a partially crosslinked polysaccharide solution and the second part comprising a further crosslinker for the polysaccharide, wherein the polysaccharide or further crosslinker comprise chitosan or a chitosan derivative;
b) applying the mixed parts as a fluid directed onto the body tissue or structure to form a protective layer thereon.

The disclosed composition, protective layer and method are especially useful for treating mucosal tissues in the ears, nose or throat and openings, recesses, passageways or joints in the limbs or spinal column. In a preferred embodiment the applied composition will not drip or run from a target area to which it has been spray-applied. By employing a partially crosslinked polysaccharide and mixing it with a further crosslinker to form a low viscosity or semi-viscous fluid rather than a much more viscous, non-sprayable gel, a sprayable composition may be dispensed through a spray device in fluid form, applied to a target area to form a fluid or only recently gelled protective layer, and kept substantially or completely in place on the target area. This approach can avoid use of more rapidly curing but potentially less bioacceptable crosslinkers at the target area. If desired, a less bioacceptable crosslinker may also be employed, but at a significantly reduced concentration compared to the concentration which might have been needed if the starting polysaccharide solution had not been partially crosslinked.

BRIEF DESCRIPTION OF THE DRAWING

Like reference symbols in the various figures of the drawing indicate like elements. The elements in the drawing are not to scale.

DETAILED DESCRIPTION

Figure 1:
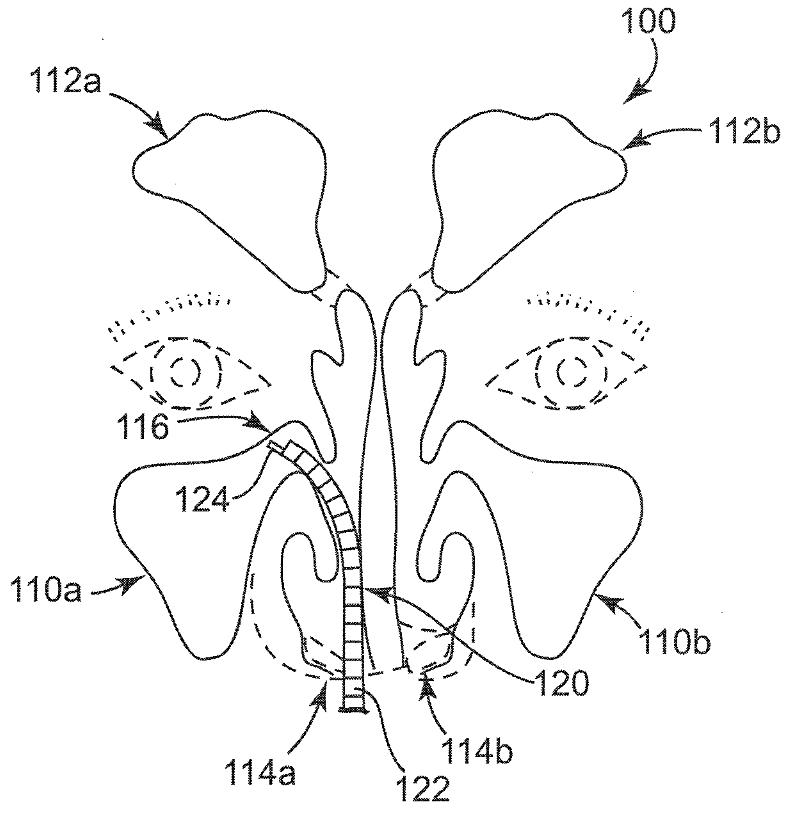
FIG. 1 is a schematic view showing the disclosed method.

The following detailed description describes certain embodiments and is not to be taken in a limiting sense. All weights, amounts and ratios herein are by weight, unless otherwise specifically noted. The terms shown below have the following meanings:

The term "adhesion" refers to the sticking together of a body structure or prosthetic material to tissue, to the sticking together of tissue to tissue with which it is in intimate contact for extended periods, or to the formation of tissue that connects body structures, prosthetic materials or tissues to one another across a normally open space.

The term "antimicrobial" refers to an ability to cause greater than a 90% numeric reduction (viz., at least a 1-log order reduction) in a population of one or more of *Staphylococcus aureus, Pseudomonas aeruginosa, Streptococcus pneumonia, Haemophilus influenzae* or *Moraxella catarrhalis.*

The terms "attached" and "adhered" when used in reference to a bacterial biofilm and a surface mean that the biofilm is established on and at least partially coats or covers the surface, and has some resistance to removal from the surface. As the nature of this relationship is complex and poorly understood, no particular mechanism of attachment or adherence is intended by such usage.

The term "bacterial biofilm" means a community of bacteria attached to a surface, with the organisms in the community being contained within an extracellular polysaccharide (EPS) matrix produced by the bacteria.

The term "biocompatible" when used in reference to a substance means that the substance presents no significant deleterious or untoward effects upon the body.

The term "biodegradable" when used in reference to a substance means that the substance will degrade or erode in vivo to form smaller chemical or physical species. Such degradation process may be enzymatic, chemical or physical.

The term "bioresorbable" when used in reference to a substance means that the substance is capable of being absorbed by the body.

The term "body temperature" when used in reference to a mammal means the normal rectal temperature (for example, for a human about 37° C.; for a cat, cow, dog or horse about 38° C.; and for a sheep about 39° C.).

The term "cohesive" when used in reference to a liquid or gel means that the liquid or gel when placed on a level surface will tend to (but need not in all cases) stick to itself and form a unitary mass.

The term "comminuted" when used in reference to a particulate material means that the particles have been fractured and reduced in size by cutting, grinding, pulverizing, triturating or other particle fracturing process employing externally-applied force.

The term "conformal" when used in reference to a composition applied to tissue or other body structure means that the composition can form a substantially continuous layer over an area to which the composition has been applied.

The terms "detaching", "removing" and "disrupting" when used in reference to a bacterial biofilm attached or adhered to a surface mean that at least a significant amount of the biofilm initially present on the surface no longer is attached or adhered to the surface. No particular mechanism of detachment, removal or disruption is intended by such usage.

The term "fluid" when used in reference to a substance means that the substance is a liquid having a loss modulus (G") greater than its storage modulus (G') and a loss tangent (tan δ) greater than 1.

The term "further crosslinker" means a crosslinker employed in the second part of the disclosed two-part composition, and which is capable of crosslinking the disclosed partially crosslinked polysaccharide.

The term "gel" when used in reference to a substance means that the substance is deformable (viz., is not a solid), G" is less than G' and tan δ is less than 1.

The term "gelation" when used with respect to formation of a gel layer means the time at which G" equals G' and tan δ equals 1.

The term "hemostat" means a device or material which stops blood flow or promotes clotting.

The term "hydrogel" when used in reference to a gel means that the gel is hydrophilic and contains water.

The term "hydrated" when used in reference to a device or substance means that the device or substance contains uniformly distributed chemically-bound water. A "fully hydrated" device or substance is incapable of taking up additional water of hydration. A "partially hydrated" device or substance is capable of taking up additional water of hydration.

The term "inner ear" means the semicircular canals and cochlea.

The term "middle ear" means the region defined by the tympanic membrane, interior structures such as the ossicular chain, the surrounding lining and bordering structures such as the mastoid.

The term "mucoadhesive" when used in reference to a device or substance means that the device or substance will adhere to the mucus covering epithelia.

The term "nasal or sinus cavities" refers to the various tissues defining the normally air-filled passages and chambers within the nose and sinus including but not limited to the nostrils or nares, the nasal concha or turbinates, the frontal, ethmoid, sphenoid and maxillary sinuses, the sinus ostia and the nasopharnyx.

The term "partial crosslinker" means a crosslinker capable of crosslinking a polysaccharide so as to form a partially crosslinked polysaccharide.

The term "partially crosslinked" when used in reference to a polysaccharide means that two or more molecules of the polysaccharide have been joined to form an oligomeric or polymeric moiety which is a fluid when hydrated and which is capable of further crosslinking in situ.

The term "polysaccharide" includes derivatives of polysaccharides and modified polysaccharides, as well as derivatives of individual polysaccharide species and modified individual polysaccharide species. For example, the term "carboxymethylcellulose" includes carboxymethylcellulose derivatives and modified carboxymethylcelluloses, the term "chitosan" includes chitosan derivatives and modified chitosans, and the term "starch" includes starch derivatives and modified starches.

The term "protective" when used in reference to a layer of a composition atop tissue or other body structure means that the layer may assist in returning an injured, inflamed or surgically repaired tissue surface to a normal state, e.g., through one or more healing mechanisms such as modulation of an inflammatory response, phagocytosis, mucosal remodeling, reciliation or other full or partial restoration of normal function.

The term "residence time" when used in reference to a protective gel layer atop tissue or other body structure means the time period during which the gel layer or portion thereof remains in place in vivo under gross observation.

The term "solvating" means to form a solution or dispersion containing a solvent or other carrier within which a solute is dissolved or suspended.

The term "substantially collagen-free" means containing a sufficiently low amount of collagen so as not to pose a potential risk of transmission of or infection with bovine spongiform encephalopathy (BSE) or variant Creutzfeldt-Jakob disease (vCJD).

The term "substantially vertical" when used in reference to a skin surface refers to a surface whose orientation is 90±10° with respect to the horizontal. This phrase is not meant to imply that the disclosed compositions are applied only to substantially vertical surfaces or only to skin surfaces. Applicants have however determined that a substantially vertical skin surface may be used to evaluate certain rheological characteristics of the disclosed compositions during and promptly after spray application, without the need for complex instruments or other measuring devices or techniques.

The term "thin" when used in reference to a protective layer atop tissue or other body structure means having an average thickness less than about two millimeters.

Referring to FIG. 1, the disclosed method may be performed for example in the nasal or sinus cavities 100 of a patient, including the maxillary sinuses 110*a*, 110*b* and frontal sinuses 112*a*, 112*b*, which may be accessed through nares 114*a*, 114*b*. It should be noted that external features of the patient, including nares 114*a*, 114*b*, are shown in dashed lines. When the patient suffers for example from chronic rhinosinusitis, one or more treatment sites such as treatment site 116 associated with a surface of maxillary sinus 110*a* may be medically or if need be surgically addressed. Treatment site 116 includes ciliated epithelium of maxillary sinus 110*a* and may include a biofilm (not shown in FIG. 1). The treatment site need not be natural tissue and may instead be an artificial structure (not shown in FIG. 1) such as a sinus packing or stent which may also be covered at least in part with a layer of bacterial biofilm. If present, the biofilm may be removed using a solvating system (for example, the solvating system described in U.S. Patent Application Publication No. US 2007/0264310 A1) which may be applied to treatment site 116 using an introducer 120 with an articulatable delivery tube 122 containing an irrigation duct (hidden in FIG. 1) through which the solvating system may flow to a nozzle 124 at the distal end of introducer 122 and thence to the treatment site. The solvating system and residues of the biofilm may be removed from the treatment site via an aspiration duct (hidden in FIG. 1). The disclosed composition containing partially crosslinked polysaccharide and further crosslinker may likewise be applied at the treatment site using the same or a different irrigation duct in introducer 120. Those skilled in the art will appreciate that the disclosed composition (and if used, the solvating system) may be applied to the treatment site using other methods or devices. Exemplary other methods include power spray or other spray application, lavage, misting, mopping, wicking, dripping, injecting and trephination and exemplary other devices include spray nozzles (e.g., single component or multiple component spraying nozzles) and syringes (e.g., single barrel or multiple barrel glass or plastic syringes and bulb syringes). The treatment method may also be performed in other parts of the body. The treatment method has particular utility in non-vascular applications, including treatment of tissues (e.g., mucosal tissues) or structures in or near the ears, throat, limbs or spinal column.

Figure 2:
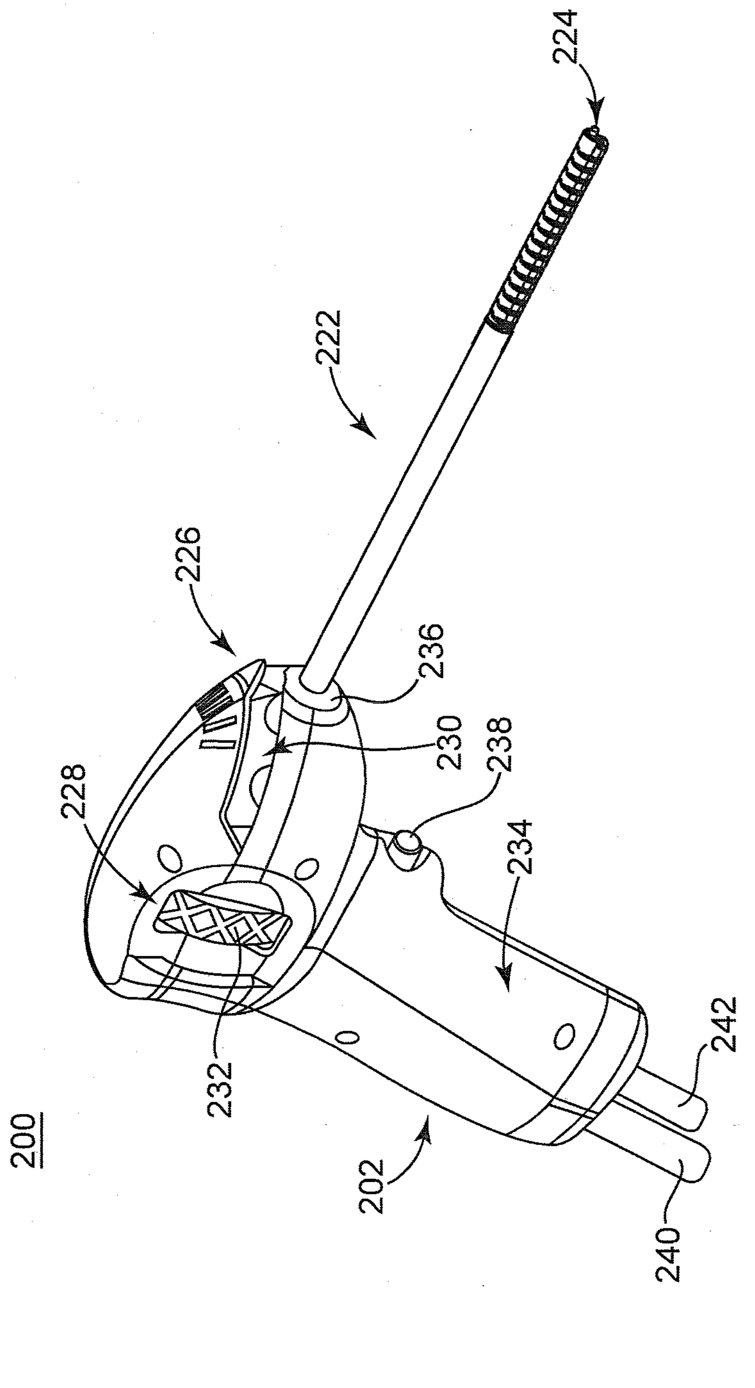
FIG. 2 is a perspective view of an instrument which may be used in the disclosed method.

FIG. 2 shows an exemplary instrument 200 which may be used in the disclosed treatment method. Instrument 200 includes a handle 202 and an introducer 222 whose distal end 224 (referenced generally) includes a spray nozzle, irrigation and aspiration ducts (not separately numbered in FIG. 2). Instrument 200 can optionally further include a first actuator assembly 226 (referenced generally) and a second actuator assembly 228 (referenced generally). A control wheel 230 in first actuator assembly 226 may be operable by a user to effectuate bending of the introducer 222, and a control wheel 232 in second actuator assembly 228 may be operable by a user to effectuate movement or rotation relative to introducer 222 of liquid sprayed from distal end 224 of introducer 222. Handle 202 serves generally as a housing for various other components of instrument 200 and as a support for introducer 222. Handle 202 may have a pistol grip-like shape, defining a grip portion 234 and a nose 236. Grip portion 234 is sized and shaped for grasping by a user's hand, whereas nose 236 is adapted for connection to introducer 222. Trigger 238 and an associated sensor and valve (not shown in FIG. 2) may be used to control the flow of the disclosed rehydrated gel (and if used, the disclosed solvating system) through irrigation tubing 240 and thence through the spray nozzle in distal end 224 and onto the desired treatment site. Trigger 238 may be provided with a multidirectional range of motion and associated with one or more additional sensors and valves (not shown in FIG. 2) to control removal from a treatment site of the solvating system, biofilm residue and other debris through the aspiration duct in distal end 224 and thence to aspiration tubing 242. Trigger 238 may also be used to control the flow of the disclosed rehydrated gel through a separate lumen in irrigation tubing 240 and thence through the spray nozzle in distal end 224 and onto the desired treatment site.

Figure 3:
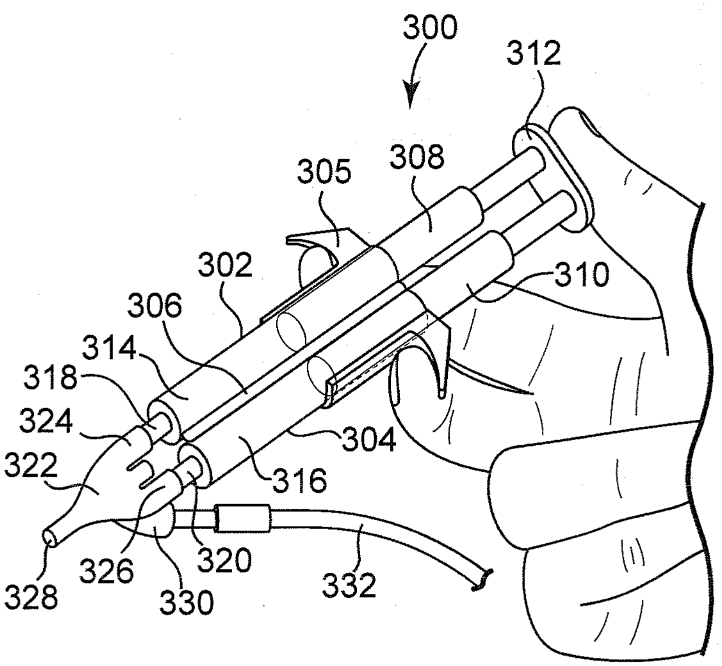
FIG. 3 is a perspective view of a dispenser which may be used in the disclosed method.

FIG. 3 shows an exemplary dispenser 300 which may be used in the disclosed method. Dispenser 300 includes pair of syringe bodies 302 and 304 embraced by grip 305, joined at central spine 306 and respectively containing piston type plungers 308 and 310. Plungers 308 and 310 are joined by a common push flange 312 which enables simultaneous actuation of plungers 308 and 310. Syringe bodies 302 and 304 respectively contain the partially crosslinked polysaccharide 314 and further crosslinker 316. Polysaccharide 314 normally is provided in dry, e.g., lyophilized form for shipment and storage, and is hydrated at the time of use. Further crosslinker 316 may (depending on the chosen further crosslinker and its storage stability) be provided in dry or hydrated form for shipment and storage, and if provided in dry form is hydrated at the time of use. When polysaccharide 314 or further crosslinker 316 are to be hydrated, this may for example be carried out by withdrawing plungers 308 and 310 while drawing water or other suitable aqueous solvent (e.g., phosphate buffered saline, or "PBS") into one or both of syringe ports 318 and 320 and then allowing or causing the contents of syringe bodies 302 and 304 to become suitably hydrated. The water or other suitable aqueous solvent may conveniently be provided in a similar companion syringe (not shown in FIG. 3) whose syringe ports are respectively joined in fluid communication with ports 318 and 320 using suitable tubing or other fittings. The contents of dispenser 300 and the companion syringe may then be passed back and forth by alternately pressing and withdrawing the respective push flanges until hydration is completed.

Dispenser 300 also includes a gas assist tip 322 whose fluid inlets 324 and 326 may respectively be coupled to syringe ports 318 and 320 and whose fluid outlet 328 may be used to direct a spray of the disclosed composition onto a desired treatment site or may be fitted with a suitable extension spray head. Gas inlet 330 may be supplied with a suitable gas (e.g., nitrogen) through tubing 332 to assist in formation of a suitable fluid spray pattern when push flange 312 is depressed. A variety of dispensers like that shown in FIG. 3 are commercially available, including the FIBRIJET™ SA-3652 and SA-6105 Gas Assisted Applicator Kits from Micromedics, Inc., and the DUPLOJECT™ applicator and TISSOMAT™ Pressure Control Device from Baxter International Inc.

The applied composition may fill the treatment site (e.g., a nasal or sinus cavity, or an opening, recess, passageway or joint in a portion of the limbs or spinal column), in which case the disclosed protective layer may be very thick with differing thicknesses throughout the layer and is not exposed to air or other nearby gases. The disclosed composition may also be applied as a thin film or other conformal coating in which case the disclosed protective layer may be relatively thin and exposed to air or other nearby gases, and with a substantially uniform thickness throughout the layer. The protective layer is a fluid and not a gel at the time of spray application, and desirably does not drip or run from the treatment site. The protective layer may later form a gel, but is not required to do so. The protective layer desirably adheres to mucosal or other natural tissues (e.g., cartilage or bone) at the treatment site and resists detachment or other disruption until natural degradation or resorption of the layer takes place, e.g., after a residence time in vivo of from one to a few (e.g., 2, 3 or 4) days, weeks or months. Meanwhile bacterial recolonization or reinfection may be significantly reduced or prevented, and improved healing and reciliation may take place. The protective layer may provide various therapeutic advantages including but not limited to bacterial adhesion repellence, anti-infective properties, local immune modulation, tissue protection, reduction or elimination of pain or bleeding, reduction in inflammation, optimization of environment for ciliary regrowth, reduction in adhesions to critical anatomy, and the like. These advantages may arise due to a variety of mechanisms including a) killing bacteria, b) inhibiting bacterial colonization, c) inhibiting the adherence of bacteria to tissue, d) reducing tissue morbidity or abscess formation, e) reducing or preventing disease recurrence (for example, specifically reducing the chronic inflammation related to bacterial toxin and EPS), f) coating and protecting tissue during healing, such as by maintenance of a moist wound which promotes platelet aggregation, or by closure of a dry wound without excessive scabrous formation, g) hemostasis, h) optimizing the environment for reciliation of the mucosa, i) speeding the growth or regrowth of cilia and j) delivering therapeutic agent(s) to the treatment site. Desirably the protective layer will adhere to a portion of the mucosa while leaving the cilia in unadhered portions free to undergo natural rhythmic cilia motion (viz., cilia beating), will if desired also deliver antimicrobial agents or additional therapeutic agents, and desirably will discourage or prevent bacteria from adhering to the treatment site.

A wide variety of polysaccharides or their derivatives may be employed in the disclosed composition, protective layer and method. Exemplary polysaccharides include alginates, carrageenans, celluloses (for example, hydroxyethylcellulose, hydroxypropylcellulose, methylcellulose and hydroxypropylmethylcellulose), chitins, chitosans, chondroitin sulfates, dextrans, galactomannans, glycogens, hyaluronic acids, starches and other biocompatible polysaccharides and mixtures thereof. Chitosans (including salts and other chitosan derivatives) are especially preferred polysaccharides. Exemplary chitosans and their salts (including citrate, nitrate, lactate, phosphate, chloride and glutamate salts) may be obtained from a variety of commercial sources including KitoZyme S.A., Fluka Chemie AG, the NovaMatrix unit of FMC BioPolymer AS, Heppe Medical and Sigma-Aldrich Co. Chitosan may also be synthesized by elimination of N-acetyl groups through deacetylation of chitin (poly-N-acetyl-D-glucosamine) by hydrolysis. The resulting oligomer or polymer has a plurality of repeating units (e.g., about 2 to about 10,000 repeating units, about 60 to about 600 repeating units, or such other amount as may be desired for the chosen end use). Some or all of the repeating units will contain deacetylated amino groups (e.g., about 30 to about 100% or about 60 to about 100% of the total repeating units), with the remaining repeating units (if any) containing acetylated amino groups. Chitosan is a cationic polymer composed of glucosamine monomers, and may have a variety of number average molecular weights, e.g., about 400 to about 2000 kDa, about 10 to about 500 kDa, or about 10 to about 100 kDa. The chitosan may for example be an ultralow molecular weight material having a number average molecular weight less than about 50 kDa, a low molecular weight material having a number average molecular weight of about 50 to about 200 kDa, a medium molecular weight material having a number average molecular weight of about 200 to about 500 kDa or a high molecular weight material having a number average molecular weight greater than about 500 kDa. Chitosan derivatives may also be employed, for example derivatives in which one or more hydroxyl or amino groups have been modified for the purpose of altering the solubility or mucoadhesion characteristics of the derivative. Exemplary derivatives include thiolated chitosans, and non-thiolated chitosan derivatives such as carboxymethyl, acetylated, alkylated or sulfonated chitosans (for example O-alkyl ethers, O-acyl esters, cationized trimethyl chitosans and chitosans modified with polyethylene glycol). Chitosan derivatives may be obtained from a variety of sources. For example, thiolated chitosans may be obtained from ThioMatrix Forschungs Beratungs GmbH and Mucobiomer Biotechnologische Forschungs-und Entwicklungs GmbH or prepared by reaction of chitosan with a suitable thiolating reactant, e.g., as described in the above-mentioned Published PCT Application No. WO 03/020771 A1 or in the above-mentioned Roldo et al., Krauland et al., Bernkop-Schnürch and Bernkop-Schnürch et al. papers. Additional preferred polysaccharides include celluloses such as those listed above, chitin, chondroitin sulfate, dextran, glycogen, hyaluronic acid and starches.

The polysaccharide is partially crosslinked before being packaged and sent or otherwise provided to end users. Partial crosslinking may be performed in a variety of ways. For example, partial crosslinking may be carried out using a dehydrothermal crosslinking process in which a mass of free-flowing hydratable polysaccharide particles are individually partially crosslinked to form a mass of free-flowing hydratable partially crosslinked polysaccharide particles. Dehydrothermal crosslinking is in effect a solid state crosslinking process in which a material is exposed to one or both of heat and reduced pressure to cause initial dehydration followed by loss of additional water and formation of crosslinking bonds via an inter- or intra-molecular condensation process. It is not necessary to add external cross-linking agents, and in the case of the disclosed particles the presence of such agents may make it more difficult to retain their free-flowing nature. Dehydrothermal crosslinking desirably involves dehydrating the product to be crosslinked to a moisture content less than about 1%, and using sufficient additional heat or vacuum to achieve a desired crosslink density. For example, in the absence of vacuum, temperatures above about 80° C., above about 90° C., above about 100° C. or above about 120° C. may be employed, with higher temperatures generally providing faster reaction rates. The polysaccharide desirably is not heated to an extent sufficient to cause browning, and accordingly temperatures less than 160° C. or less than 150° C. are preferred. Fairly long heating times may be needed at ambient pressure, for example, about 40 hours at 140-150° C. plus about total 20 hours for warmup and cooldown. When reduced pressure is used, lower temperatures may be employed and a vacuum of at least about 1 mm Hg, and preferably at least about $10^{-3}$ mm Hg may be preferred. Thus the higher the temperature, the lower the required vacuum or heating time required to arrive at a given crosslink density, and vice versa. It is accordingly difficult to specify an exact heating time or range of heating times, although times of at least about 10 hours, at least about 20 hours, at least about 30 hours or about 40 to about 60 hours, and less than about 2 weeks or less than about 1 week (not counting the times required for warmup and cooldown) may be employed. In many cases it will suffice to determine the heating time, temperature and pressure empirically, for example by hydrating the dehydrothermally crosslinked particles (as described in more detail below and without adding the disclosed second part containing a further crosslinker) and spraying the resulting mass against a body temperature substantially vertical surface as shown in Example 1. If the mass is too thick to be sprayable, then the extent of partial crosslinking should be reduced. If the mass is sprayable but will not drip or run, then the extent of partial crosslinking may be left as is or if desired further reduced. Instrumentation may also be employed to measure rheological properties for the mass, e.g., to determine if a fluid or gel has been obtained, with the extent of partial crosslinking being reduced to prevent or discourage premature gel formation.

Partial crosslinking may also be carried out using a variety of external crosslinking agents, which when so used may be referred to as partial crosslinkers. Exemplary partial crosslinkers include genipin, an oxidized polysaccharide such as oxidized starch, or glutaraldehyde, with genipin being preferred due in part to its good biocompatibility and notwithstanding its somewhat slow crosslinking speed. The amount of partial crosslinker may vary widely depending upon the chosen polysaccharide and partial crosslinker. In many cases it will suffice to determine the partial crosslinker amount empirically, for example by reacting chosen amounts of the polysaccharide and partial crosslinker together, hydrating the resulting product if need be and spraying the resulting mass against a body temperature substantially vertical surface as described above.

When an oxidized polysaccharide is used as the partial crosslinker, the polysaccharide may be oxidized to an extent just sufficient to provide aldehyde groups capable of promoting partial (but not unduly complete) crosslinking of the polysaccharide. The polysaccharide may if desired be oxidized to a different (e.g., a greater) extent and an adjustment (e.g., an increase) made in the polysaccharide amount. Preferably the partial crosslinking reaction is substantially complete within a few days or hours (e.g., less than 2 days, less than 1 day, less than 12 hours or less than 8 hours) after the polysaccharide and partial crosslinker have been mixed. A wide variety of oxidized polysaccharides may be employed, including alginates, carrageenans, celluloses (e.g., hydroxyethylcellulose, hydroxypropylcellulose, methylcellulose and hydroxypropylmethylcellulose), chitins, chondroitin sulfates, dextrans, galactomannans, glycogens, hyaluronic acids, starches and other biocompatible polysaccharides capable of being oxidized. Oxidized polysaccharides such as oxidized cellulose (e.g., those mentioned above), chitin, chondroitin sulfate, dextran, glycogen, hyaluronic acid and starch are especially preferred. Representative oxidizing agents or techniques for preparing oxidized polysaccharide include the use of a) sodium periodate, b) hypochlorite ion in the presence of di-tert-alkylnitroxyl catalysts, c) metal-catalyzed oxidation, using for example ruthenium, d) anhydrous oxidation using for example nitrogen dioxide in for example a halocarbon, e) enzymatic or chemo-enzymatic oxidation of starch, guar and other polysaccharides, f) 2,2,6,6-tetramethylpiperidine-1-oxyl (TEMPO) catalyzed oxidation with mild oxidants such as dimethylsulfoxide (DMSO) or diacetoxyiodobenzene, and other oxidation agents and techniques that will be known to persons having ordinary skill in the art. Depending on the selected oxidizing agent or technique, a variety of degrees of oxidation, degrees of polymerization and oxidation sites may be employed. For example, oxidation may be directed at a primary hydroxyl group (for example, the 6-hydroxyl group in the anhydroglucose units of glucans), resulting in carboxyl-polysaccharides with preserved ring structures. Oxidation may also be directed at a vicinal diol function present in a monosaccharide ring (for example, the C2-C3 site in anhydroglucose units), resulting in cleavage of the monosaccharide units and the production of dialdehyde functional groups. The dialdehyde content of such an oxidized polysaccharide may range from a degree of oxidation of, for example, 2% to virtually 100%, e.g., more than 30% or more than 50% of the available oxidation sites. The oxidized polysaccharide may also contain other functional groups, for example hydroxyalkyl groups, cationic groups, carboxyl groups and other acid groups. As a generalization, reduced amounts of oxidized polysaccharide may be employed as the partial crosslinker as the degree of polysaccharide oxidation is increased.

When a composition containing a mixture of two or more particulate polysaccharides is employed, one or more than one of the polysaccharide particulates may be partially crosslinked. This permits customization of properties such as fluid behavior, spraying characteristics, eventual gelation time (if any) and degradation rate following placement. If desired, a blend of one or more partially crosslinked polysaccharides may be subjected to an additional partial crosslinking reaction, for example a dehydrothermal crosslinking reaction. The particles could also be kept separate and later mixed by an end user, although this will normally be less convenient than packaging the mixture in read-to-use or close to ready-to-use form at a manufacturing site.

The polysaccharide desirably is provided in dry particulate form, for example, as free-flowing granules whose average particle diameter is less than about 1 mm, less than about 100 μm, about 1 to about 80 μm, or less than 1 μm. Doing so can help reduce degradation during prolonged storage.

The polysaccharide normally will be hydrated just prior to mixing with the further crosslinker and placing the resulting fluid mixture in a treatment site. Hydration may be carried out by dissolving the polysaccharide in water or an aqueous solution containing any other desired ingredients. For example, normal saline solution and PBS are preferred and readily available hydration solutions. The amount of polysaccharide in the hydrated solution may depend in part on the polysaccharide molecular weight, and may for example be about 1 to about 20%, about 1 to about 10% or about 1 to about 5% based on the solution weight. Copending U.S. Provisional Application Ser. No. 61/047,580, filed Apr. 24, 2008, describes a preferred technique for rehydrating dehydrothermally crosslinked polysaccharide particles, by dispersing the particles in a biocompatible water-miscible polar dispersant, and combining the dispersion with sufficient aqueous solvent for the particles to convert them to a cohesive hydrogel. This technique may be adapted for use in the present invention, using polysaccharide particles that have been partially crosslinked to an extent sufficient so that a fluid rather than a hydrogel will form following hydration. It can be difficult when hydrating polysaccharide particles to obtain a smooth, fluid mixture due to the tendency of some dry powdered materials to form clumps when combined with water. Clumping may however be avoided by dispersing the polysaccharide particles in a biocompatible water-miscible polar dispersant, followed by mixing the dispersion with sufficient aqueous particle solvent (viz., a water-based solvent for the particles) to convert the particles to a clump-free fluid solution. The dispersant is a sufficiently poor solvent for the particles so that the mixture of particles and dispersant will not form a true solution. The particles in such a dispersion desirably are sufficiently small so that the dispersion is stable or quasi-stable (e.g., a colloidal dispersion or a reasonably persistent suspension) after the particles and dispersant have been agitated, e.g., by swirling them together. Without being bound by theory, the addition of the aqueous particle solvent is believed to permit hydration to occur approximately simultaneously at the surface of each suspended particle via dissolution of the surrounding dispersant into the aqueous particle solvent phase, thereby permitting formation of a fluid solution without forming visible clumps of unhydrated polysaccharide. In this fashion a dispersed polysaccharide may be combined with water or an aqueous solution to form a clump-free fluid solution even though the dry powdered polysaccharide would not ordinarily do so. The disclosed mixing method may for example be used to prepare a satisfactory clump-free fluid using passage between two syringes as described above in connection with FIG. 3, mild agitation or other simple mixing techniques and without requiring the use of a mechanical stirrer. The disclosed mixing method may also permit formation of very concentrated fluid solutions which could not be obtained by merely mixing a powdered polysaccharide with water or acidified water. The polysaccharide may be comminuted but desirably is non-comminuted.

The selection of dispersant and aqueous particle solvent may depend upon the chosen polysaccharide. For polysaccharides such as chitosan which have relatively poor solubility in pure water but which become soluble when the water is acidified, deionized water may be used as the dispersant and acidified water may be used as the aqueous particle solvent. Other combinations of dispersant and aqueous solvent may also be used. For example, ethanol, isopropanol or acetone may be used as the dispersant for many polysaccharides (including chitosan and blends containing chitosan) and deionized water, normal saline solution or PBS may be used as the aqueous particle solvent.

A variety of further crosslinkers may be used in the second part of the disclosed composition, and in the disclosed protective layer and method. The further crosslinker desirably is relatively fast-acting so as to provide a two-part composition that will not drip or run if the two parts are mixed and sprayed on a body temperature vertical surface. Exemplary further crosslinkers include oxidized polysaccharides, chitosan and glutaraldehyde, with oxidized polysaccharides being preferred. Oxidized polysaccharides appear to provide especially rapid crosslinking while avoiding the use of potentially less bioacceptable low molecular weight aldehydes. The aldehyde groups in an oxidized polysaccharide may also enhance mucoadhesion. Oxidized polysaccharides may provide additional benefits including improved or better controlled biodegradability, bioresorbability, drug delivery or haemostatic properties. A wide variety of oxidized polysaccharides may be employed, including those discussed above in connection with the partial crosslinker. Oxidized polysaccharides such as oxidized cellulose, chitin, chondroitin sulfate, dextran, glycogen, hyaluronic acid and starch are especially preferred. When an oxidized polysaccharide is used as the further crosslinker, the polysaccharide desirably is oxidized to an extent sufficient to provide aldehyde groups capable of promoting rapid further crosslinking of the partially crosslinked polysaccharide when the polysaccharide and oxidized polysaccharide are combined in aqueous solution. Representative oxidizing agents or techniques and representative degrees of oxidation include those discussed above in connection with the partial crosslinker.

The partial crosslinker and further crosslinker may be the same or different, with for example a small amount of partial crosslinker being used to prepare the partially crosslinked polysaccharide, followed by the use of a larger amount of the same crosslinker as the further crosslinker in the disclosed two-part composition. For example, glutaraldehyde or chitosan may be used as both the partial and further crosslinker.

The further crosslinker desirably is dissolved in water or another suitable solvent prior to use. Recommended further crosslinker types and amounts typically will depend on the further crosslinker molecular weight, the type and amount of partially crosslinked polysaccharide and the availability of remaining sites for crosslinking therein. The further crosslinker amount may for example be about 1 to about 20%, about 1 to about 10% or about 1 to about 5% of the disclosed second part.

Selection of the type and amount of partially crosslinked polysaccharide and further crosslinker desirably takes into account the likely minimum and maximum times that may be required for mixing the first and second parts and spraying or otherwise directing the resulting mixture onto body tissue or structure. Premature gel formation may be estimated by placing water (e.g., 100 mL) optionally combined with a suitable crosslinking quencher (e.g., glucosamine) into a suitable vessel, preparing a fresh mixture of the first and second parts and an optional water-soluble colorimetric dye (e.g., a dye such as is listed below), and promptly spraying the mixture downwardly over a short aerial distance (e.g., a few mm) onto the water surface and observing whether or not gel particles are formed or dye traces become visible in the water.

The polysaccharide or further crosslinker contain chitosan or a chitosan derivative. Two-part compositions in which the first part contains a partially crosslinked chitosan and the second part contains an oxidized chitosan may also be prepared.

The disclosed compositions desirably are substantially collagen-free. Preferably the compositions are sufficiently free of collagen (e.g., containing no collagen at all) so as to be saleable worldwide for use without restriction in humans.

The disclosed composition typically will be subjected to sterilization and placed in suitable sealed packaging (for example, a multicomponent syringe, a vial or vials, or a multi-chamber pouch made of suitable materials) prior to shipment to an end user. Additional property customization may be carried out by using a sterilization procedure such as gamma radiation or electron beam (E-Beam) processing to cause controlled chain scission. Cold ionizing radiation sterilization (e.g., cold E-Beam sterilization) may be employed to limit the degree of chain scission, as discussed in PCT Application No. PCT/US2009/041593, filed even date herewith. Whether or not sterilized, the first part containing the partially crosslinked polysaccharide normally will be kept separate from the second part containing the further crosslinker until just prior to use.

The partially crosslinked polysaccharide and further crosslinker may for example be combined in a molar ratio of about 20:1 to about 1:20, about 10:1 to about 1:10, about 5:1 to about 1:10, about 3:1 to about 1:5 or about 20:1. Once the first and second part have been mixed, the further crosslinking reaction preferably is substantially complete within a few minutes (e.g., less than 5 minutes, less than 3 minutes, less than 2 minutes or less than 1 minute) after the start of mixing, yielding an initially fluid protective layer that desirably will not drip or run from a target area on a body temperature vertical skin surface. The presence of phosphate ions appears to accelerate the crosslinking reaction. Phosphate may be provided by using PBS as a solvent for one or both of the partially crosslinked polysaccharide and the further crosslinker.

The disclosed composition and protective layer may optionally include a variety of other ingredients before or after hydration. Exemplary other ingredients include non-aqueous solvents, acids, bases, buffering agents, antimicrobial agents, therapeutic agents and other adjuvants. An acid, base or buffering agent may for example maintain the composition, protective layer or both at an appropriate pH for contacting human tissue, e.g., a pH greater than 4.5, a near-neutral pH, or a pH less than 8.5. Exemplary buffering agents include barbitone sodium, glycinamide, glycine, potassium chloride, potassium phosphate, potassium hydrogen phthalate, sodium acetate, sodium citrate, sodium phosphate and their conjugate acids.

The disclosed compositions desirably are inherently antimicrobial without requiring addition of a separate antimicrobial agent. Antimicrobial activity may be influenced by the proportion of chitosan or chitosan derivatives in the composition (with higher proportions tending to provide greater antimicrobial activity) and by the number of available chitosan amine groups. Accordingly, use of chitosan derivatives containing low numbers of available amino hydrogen atoms (such as the N-carboxyethyl derivatives desired in the above-mentioned Weng et al. paper) may be contraindicated. In any event, a separate antimicrobial agent may be employed if desired. A useful list of such antimicrobial agents may be found, for example, in the above-mentioned U.S. Patent Application Publication No. US 2007/0264310 A1.

Exemplary therapeutic agents which may be employed in the disclosed compositions include any material suitable for use at the intended treatment site including analgesics, anti-cholinergics, anti-fungal agents, antihistamines, steroidal or non-steroidal anti-inflammatory agents, anti-parasitic agents, antiviral agents, biostatic compositions, chemotherapeutic/antineoplastic agents, cytokines, decongestants, hemostatic agents (e.g., thrombin), immunosuppressors, mucolytics, nucleic acids, peptides, proteins, steroids, vasoconstrictors, vitamins, mixtures thereof, and other therapeutic materials that will be known to those skilled in the art. A useful list of such therapeutic agents may be found, for example, in the above-mentioned U.S. Patent Application Publication No. US 2007/0264310 A1.

Other adjuvants that may be included in the disclosed compositions include dyes, pigments or other colorants (e.g., FD & C Red No. 3, FD & C Red No. 20, FD & C Yellow No. 6, FD & C Blue No. 2, D & C Green No. 5, D & C Orange No. 4, D & C Red No. 8, caramel, titanium dioxide, fruit or vegetable colorants such as beet powder or beta-carotene, turmeric, paprika and other materials that will be known to those skilled in the art); indicators; flavoring or sweetening agents including but not limited to anise oil, cherry, cinnamon oil, citrus oil (e.g., lemon, lime or orange oil), cocoa, eucalyptus, herbal aromatics (e.g., clove oil, sage oil or cassia oil), lactose, maltose, menthol, peppermint oil, saccharine, sodium cyclamate, spearmint oil, sorbitol, sucrose, vanillin, wintergreen oil, xylitol and mixtures thereof, antioxidants; antifoam agents; and rheology modifiers including thickeners and thixotropes. The disclosed compositions desirably do not contain ingredients which might potentially harm mucosal tissues or structures, e.g., tissues in the nasal or sinus cavities.

In those instances where it is desirable to remove water from tissue, e.g., to remove fluid from polyps or edematous tissue, a hypertonic agent may be employed in the disclosed compositions. Exemplary hypertonic agents include furosemide, sodium chloride gel and other salt preparations that draw water from tissue or substances which directly or indirectly change the osmolar content of the mucous layer. Where sustained release or delayed release of a therapeutic agent is desirable, a release agent modifier may also be included.

The disclosed compositions may desirably be used as a part of a multi-step treatment regimen which disrupts a bacterial biofilm and discourages its return. For example, a series of steps that may be broadly classified as Cleansing/Disrupting, Killing, Aerating, Protecting/Coating, and Healing may be carried out. These various steps may be performed in a variety of sequences, e.g., the order in which the Killing and Aerating steps are performed may be reversed. The Cleansing/Disrupting step may be carried out by administering a solvating system as discussed above in connection with FIG. 1 and FIG. 2. The Killing step may be carried out by applying a suitable antimicrobial agent to the treatment site. This may for example be accomplished by including an antimicrobial agent in the solvating system, as a separately-applied composition, or in both the solvating system and in a separately-applied composition. An antimicrobial agent may also be applied or administered post operatively. The Aerating step may be carried out by providing air passageways or improving air passageways to the treated tissues by opening occluded or partially occluded passages, e.g., the sinuses or sinus ostia for nasal applications. This may for example be accomplished by surgically removing obstructive tissue structures or by manually displacing such structures. The Protecting/Coating step may be carried out by coating at least part of the thus-treated tissue with the disclosed protective layer containing partially crosslinked polysaccharide and further crosslinker as described above. The Healing step may be carried out by allowing the cleansed, protected and sealed tissue surface to undergo a return to a normal state, e.g., through one or more healing mechanisms such as modulation of an inflammatory response, phagocytosis, mucosal remodeling, reciliation or full or partial restoration of normal function. The multi-step treatment regimen may include or be followed by a Clearing step in which the disclosed protective layer containing partially crosslinked polysaccharide and further crosslinker is sufficiently biodegradable or bioresorbable to disappear from the treatment site in a desired time period, e.g., more than 1 day, more than 3 days, about 4 to 7 days or about 7 to 28 days, and desirably without shedding large solid chunks. The disclosed method may advantageously be accomplished without requiring surgery, for example by applying and removing the optional solvating system and by applying the disclosed protective layer through normal aspiration/suction techniques or by simple flushing of affected tissue. A comparable series of steps may be performed in a multi-step treatment regimen in a portion of the middle or inner ear. Further details regarding such a regimen may be found in U.S. Patent Application Publication No. US 200710264310 A1.

The invention is further illustrated in the following non-limiting examples.

EXAMPLE 1

Partial Crosslinking Using Oxidized Polysaccharides

Chitosan solutions were prepared by dissolving varying amounts of chitosan glutamate (PROTASAN™ UP G 113 from the NovaMatrix unit of FMC BioPolymer AS, or "G 113") in water or PBS. An oxidized methylcellulose ("OXMC") solution was prepared by reacting a partially oxidized methylcellulose (MO387 from Sigma Aldrich Company) with sodium periodate. The solutions were mixed in various ratios and concentrations, poured into glass Petri dishes, and lyophilized by freeze drying to provide white foamy products. The lyophilized products were immersed in water and observed to determine the qualitative rate of water uptake. The results are shown below in Table 1.

TABLE 1

| Run No. | Chitosan Solution | Oxidized Polysaccharide Solution | Chitosan:Oxidized Polysaccharide Ratio | Water Uptake Rate |
|---|---|---|---|---|
| 1 | 5% G 113 in PBS | 5% OXMC in PBS | 1:10 | Slow Uptake |
| 2 | 5% G 113 in water | 2.5% OXMC in water | 1:10 | Quick Uptake |
| 3 | 5% G 113 in PBS | 2.5% OXMC in water | 1:5 | Dissolves |
| 4 | 5% G 113 in PBS | 5% OXMC in PBS | 1:2 | Slow Uptake |

Additional formulations were similarly prepared using oxidized hydroxypropylmethylcellulose (made from 442755 partially oxidized hydroxypropylmethylcellulose from Sigma Aldrich Company) rather than oxidized methylcellulose. These exhibited quicker water uptake.

The lyophilized products shown in Table 1 exhibited varying degrees of crosslinking, with the Run No. 1 formulation having the highest degree of crosslinking and the Run No. 4 formulation the lowest. The resulting hydrated products could be combined with a further crosslinker such as genipin and sprayed or injected onto or into a treatment site.

EXAMPLE 2

Partial Crosslinking Using Glutaraldehyde

A 1.5 mL portion of a 5% solution of G113 chitosan glutamate in PBS and a 1.5 mL portion of a 0.015% glutaraldehyde solution in PBS were each placed into 3 mL single barrel syringes. The syringe tips were connected using a cannula and the contents were mixed until homogenous by alternately pressing and withdrawing the two syringe plungers. The mixture was allowed to stand overnight. The resulting partially crosslinked polysaccharide contained the reaction product of a 2.5% chitosan glutamate solution with 75 ppm glutaraldehyde.

EXAMPLE 3

Spray Application

A solution of dialdehyde starch (No. 9056>80% oxidized starch from Monomer-Polymer & Dajac Labs, Inc.) in PBS was lyophilized and then hydrated by dissolving the lyophilized product in sufficient deionized water to provide a further crosslinker solution containing 5% oxidized starch. Using a gas-assisted applicator (FIBRIJET SA-6030 regulator, from Micromedics, Inc., controlling a FIBRIJET SA-3652 spray set equipped with a pair of 3 cc syringes), the partially crosslinked polysaccharide solution from Example 2 and the 5% oxidized starch solution were spray-applied at a 1:1 ratio onto a vertically-oriented human hand to observe setting time and adherence to a body temperature substantially vertical tissue surface. About 3-4 mL of the mixture was sprayed to form a fluid protective layer. The composition exhibited good spray characteristics, appeared to adhere well to and cover the landing site in a thin, conformal film, and did not drip, sag or run. The resulting protective layer was sticky, flexible, well adhered and became slick when exposed to water. Scrubbing was required to remove the protective layer.

In a comparison run, the partially crosslinked polysaccharide solution was replaced by a 2.5% chitosan glutamate solution which had not been partially crosslinked. The spray-applied coating began running and dripping shortly after landing. The coating was initially thin and watery, and reached a sticky, non-runny state about 16 seconds after spraying. The coating appeared to be less firm and less solid than the coating prepared using a partially crosslinked polysaccharide.

EXAMPLE 4

Partial Crosslinking Using Chitosan

Using the method of Example 2, oxidized methylcellulose solutions were prepared in uncrosslinked and partially crosslinked forms using varying amounts of chitosan glutamate as the partial crosslinker. A 15% oxidized methylcellulose solution was made by reacting MO387 methylcellulose (Sigma-Aldrich Co.) with sodium periodate in deionized water. The reaction product was subsequently lyophilized and rehydrated in PBS. A 0.5 mL portion of this solution was placed in a 3 mL syringe and mixed with a syringe containing a 0.5 mL portion of a 0.3% G113 chitosan glutamate solution in PBS, de-aerated, and allowed to stand for 24 hours, thereby providing a partially crosslinked polysaccharide containing 7.5% oxidized methylcellulose reacted with 0.15% chitosan (Solution A). In similar fashion, a 0.5 mL portion of the methyl cellulose solution was mixed with a syringe containing a 0.5 mL portion of a 0.5% G113 chitosan glutamate solution in PBS, thereby providing a partially crosslinked polysaccharide containing 7.5% oxidized methylcellulose reacted with 0.25% chitosan (Solution B). A non-crosslinked 7.5% oxidized methylcellulose solution was prepared as a control (Solution C).

Using the method of Example 3, Solutions A, B and C were spray-applied at a 1:1 ratios with 5% G113 chitosan glutamate solution in PBS onto a vertically-oriented human hand. About 2 mL of each mixture was sprayed to form a fluid protective layer. The compositions made using Solutions A and B exhibited good spray characteristics, appeared to adhere well to and cover the landing site in a thin, conformal film, and did not drip, sag or run. The composition made using Solution B appeared to form a slightly more solid protective layer than the composition made using Solution A. Both protective layers were sticky, flexible, well adhered and became slick when exposed to water. Scrubbing was required to remove the coating.

The composition made using Solution C began to run shortly after application, and stopped running and appeared to have set about 20-30 seconds after spraying.

The results set out above show that partially crosslinked polysaccharides may be combined with further crosslinkers to prepare fluid, sprayable mixtures which quickly form thin, conformal fluid protective layers in situ on a body temperature substantially vertical tissue surface. The formulations were in each instance sprayable, antibacterial, biodegradable or bioresorbable and capable of serving as a scaffold for drug delivery.

In addition to a two-part composition, the first part comprising a partially crosslinked polysaccharide and the second part comprising a further crosslinker for the polysaccharide, wherein the polysaccharide or further crosslinker comprise chitosan or a chitosan derivative and the composition when hydrated and mixed can be delivered as a fluid through a spray applicator to provide a thin, conformal protective layer on a body temperature substantially vertical skin surface, other embodiments of the invention include like compositions:

- wherein the polysaccharide comprises chitosan or a chitosan derivative;
- wherein the further crosslinker comprises chitosan or a chitosan derivative;
- wherein the polysaccharide and further crosslinker comprise chitosan or a chitosan derivative;
- wherein the polysaccharide or further crosslinker comprise cellulose or a cellulose derivative;
- wherein the polysaccharide or further crosslinker comprise starch or a starch derivative;
- wherein the polysaccharide or further crosslinker comprise chitin, chondroitin sulfate, dextran, glycogen, hyaluronic acid or derivative thereof;
- wherein the polysaccharide and further crosslinker are combined in a molar ratio of about 20:1 to about 1:20;
- wherein the polysaccharide and further crosslinker are combined in a molar ratio of about 3:1 to about 1:5;
- further comprising phosphate ions;
- packaged in a syringe;
- wherein the polysaccharide is in dry particulate form; and
- wherein the composition when hydrated and mixed can be spray-applied to form a thin, conformal, initially fluid protective layer on a body temperature substantially vertical skin surface, and does not drip or run from the surface when so applied.

In addition to a protective layer on a body temperature surface, the layer comprising an initially fluid mixture of a partially crosslinked polysaccharide and a further crosslinker for the polysaccharide, wherein the polysaccharide or further crosslinker comprise chitosan or a chitosan derivative and the partially crosslinked polysaccharide was partially crosslinked before mixture with the further crosslinker, other embodiments of the invention include like protective layers:

- wherein the polysaccharide comprises chitosan or a chitosan derivative;
- wherein the further crosslinker comprises chitosan or a chitosan derivative;
- wherein the polysaccharide and further crosslinker comprise chitosan or a chitosan derivative;
- wherein the polysaccharide or further crosslinker comprise cellulose or a cellulose derivative;
- wherein the polysaccharide or further crosslinker comprise starch or a starch derivative;
- wherein the polysaccharide or further crosslinker comprise chitin, chondroitin sulfate, dextran, glycogen, hyaluronic acid or derivative thereof; and
- wherein the layer does not drip or run from the surface.

In addition to a method for treating body tissue or structure, which method comprises:

- a) mixing a two-part composition, the first part comprising a partially crosslinked polysaccharide solution and the second part comprising a further crosslinker for the polysaccharide, wherein the polysaccharide or further crosslinker comprise chitosan or a chitosan derivative;
- b) applying the mixed parts as a fluid directed onto the body tissue or structure to form a protective layer thereon, other embodiments of the invention include like methods:

- comprising mixing the composition using a multiple-barrel syringe;
- comprising applying the fluid by spraying;
- comprising applying the fluid to a nasal cavity;
- comprising applying the fluid to a sinus cavity;
- comprising applying the fluid to a middle or inner ear;
- comprising applying the fluid to an opening, recess, passageway or joint in a limb;
- comprising applying the fluid to an opening, recess, passageway or joint in a spinal column;
- wherein the mixed parts do not drip or run from the tissue or structure;
- wherein the polysaccharide comprises chitosan or a chitosan derivative;
- wherein the further crosslinker comprises chitosan or a chitosan derivative;
- wherein the polysaccharide or further crosslinker comprise cellulose or a cellulose derivative;
- wherein the polysaccharide or further crosslinker comprise starch or a starch derivative;
- wherein the polysaccharide or further crosslinker comprise chitin, chondroitin sulfate, dextran, glycogen, hyaluronic acid or derivative thereof; and
- wherein the composition further comprises phosphate ions.

Although specific embodiments have been illustrated and described herein for purposes of description of the preferred embodiments, it will be appreciated by those of ordinary skill in the art that a wide variety of alternate or equivalent implementations calculated to achieve the same purposes may be substituted for the specific embodiments shown and described without departing from the scope of the present invention. This application is intended to cover any adaptations or variations of the preferred embodiments discussed herein. Therefore, it is manifestly intended that this invention be limited only by the claims and the equivalents thereof.

We claim:

1. A two-part composition, the first part comprising a sterilized crosslinked polysaccharide in sealed packaging and the second part comprising a sterilized further crosslinker for the polysaccharide in sealed packaging, wherein the polysaccharide or further crosslinker comprise a biocompatible chitosan, the polysaccharide and further crosslinker are in a molar ratio of about 20:1 to about 1:20 and the two parts when hydrated are sprayable fluids deliverable through a spray applicator and reacting with one another to provide a thin, conformal, non-dripping protective layer when sprayed on a body temperature substantially vertical skin surface.

2. A composition according to claim 1 wherein the polysaccharide comprises a chitosan.

3. A composition according to claim 1 wherein the further crosslinker comprises a chitosan.

4. A composition according to claim 3 wherein the polysaccharide and further crosslinker comprise a chitosan derivative or modified chitosan.

5. A composition according to claim 1 wherein the polysaccharide or further crosslinker comprise a cellulose.

6. A composition according to claim 1 wherein the polysaccharide or further crosslinker comprise a starch.

7. A composition according to claim 1 wherein the polysaccharide or further crosslinker comprise chitin, chondroitin sulfate, dextran, glycogen or hyaluronic acid.

8. A composition according to claim 1 wherein the polysaccharide and further crosslinker are in a molar ratio of about 3:1 to about 1:5.

9. A composition according to claim 1 further comprising phosphate ions.

10. A composition according to claim 1 packaged in a syringe.

11. A composition according to claim 10 wherein the polysaccharide is in dry particulate form.

12. A composition according to claim 1 wherein the protective layer forms a gel.

13. A protective layer, the layer comprising an initially fluid mixture of a crosslinked polysaccharide and a further crosslinker for the polysaccharide, wherein the layer forms a thin, non-dripping film when sprayed on a body temperature substantially vertical skin surface, the polysaccharide or further crosslinker comprise a biocompatible chitosan and the crosslinked polysaccharide is formed from a crosslinker that is different from the further crosslinker.

14. A composition according to claim 1 wherein the first part is in a first sealed package and the second part is in a second sealed package.

15. A protective layer according to claim 13 wherein the film is substantially vertical.

16. A composition according to claim 1 wherein the polysaccharide or further crosslinker comprise a chitosan derivative that is a chitosan salt or contains one or more modified hydroxyl or modified amino groups that alter solubility or mucoadhesion characteristics of the derivative.

17. A composition according to claim 16 wherein the derivative is a thiolated chitosan, carboxymethyl chitosan, acetylated chitosan, alkylated chitosan or sulfonated chitosan.

18. A composition according to claim 16 wherein the derivative is an O-alkyl ether, O-acyl ester, cationized trimethyl chitosan or a chitosan modified with polyethylene glycol.

19. A protective layer according to claim 13 wherein the polysaccharide and further crosslinker are in a molar ratio of about 20:1 to about 1:20.

20. A method for treating body tissue or structure, which method comprises:

a) mixing a two-part composition, the first part comprising a fluid crosslinked polysaccharide solution and the second part comprising a further crosslinker for the polysaccharide, wherein the polysaccharide or further crosslinker comprise a biocompatible chitosan and the polysaccharide and further crosslinker are in a molar ratio of about 20:1 to about 1:20; and b) applying the mixed parts as a fluid directed onto the body tissue or structure to form a protective layer thereon.

21. A method according to claim 20 wherein the polysaccharide or further crosslinker comprises a chitosan derivative or modified chitosan.

* * * * *